(12) United States Patent
Lam et al.

(10) Patent No.: US 9,993,575 B2
(45) Date of Patent: Jun. 12, 2018

(54) NANOENHANCED HEMOSTATIC DEVICE AND METHODS FOR MAKING A LAYER HAVING HEMOSTATIC PROPERTIES

(71) Applicants: EMORY UNIVERSITY, Atlanta, GA (US); CHILDREN'S HEALTHCARE OF ATLANTA, INC., Atlanta, GA (US)

(72) Inventors: Wilbur A. Lam, Decatur, GA (US); Anton Sidorov, Atlanta, GA (US); Zhigang Jlang, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 196 days.

(21) Appl. No.: 14/376,728

(22) PCT Filed: Mar. 4, 2013

(86) PCT No.: PCT/US2013/028832
§ 371 (c)(1),
(2) Date: Aug. 5, 2014

(87) PCT Pub. No.: WO2013/134107
PCT Pub. Date: Sep. 12, 2013

(65) Prior Publication Data
US 2014/0364712 A1 Dec. 11, 2014

Related U.S. Application Data

(60) Provisional application No. 61/607,249, filed on Mar. 6, 2012.

(51) Int. Cl.
| | | |
|---|---|---|
| A61L 15/16 | (2006.01) | |
| A61L 15/18 | (2006.01) | |
| A61B 5/02 | (2006.01) | |
| C01B 32/184 | (2017.01) | |
| B82Y 40/00 | (2011.01) | |
| B82Y 5/00 | (2011.01) | |
| B82Y 30/00 | (2011.01) | |

(52) U.S. Cl.
CPC ............... *A61L 15/18* (2013.01); *A61B 5/02* (2013.01); *C01B 32/184* (2017.08); *A61L 2400/04* (2013.01); *A61L 2400/12* (2013.01); *B82Y 5/00* (2013.01); *B82Y 30/00* (2013.01); *B82Y 40/00* (2013.01); *Y10S 977/734* (2013.01); *Y10S 977/842* (2013.01); *Y10S 977/931* (2013.01)

(58) Field of Classification Search
CPC ........... A61L 15/14; A61L 15/18; A61L 15/42
USPC ................................. 424/448, 449, 446, 447
See application file for complete search history.

(56) References Cited

U.S. PATENT DOCUMENTS

| | | | |
|---|---|---|---|
| 2009/0192429 A1 | 7/2009 | Daniels et al. | |
| 2009/0291124 A1* | 11/2009 | Bedard | A61L 15/18 514/1.1 |
| 2012/0100203 A1* | 4/2012 | Fang | H01M 4/131 424/443 |
| 2012/0129736 A1 | 5/2012 | Tour et al. | |
| 2012/0164433 A1 | 6/2012 | Advincula | |
| 2012/0252703 A1* | 10/2012 | Dowling | A61F 13/00017 506/37 |
| 2012/0309250 A1 | 12/2012 | Velev et al. | |

FOREIGN PATENT DOCUMENTS

RU       2314026 C2    1/2008

OTHER PUBLICATIONS

Li et al (Transfer of Large-Area raphene films for high-performacne transparent conductive electrodes; Nano Letters, 2009, vol. 9, No. 12, 4359-4363).*
Hu et al. "Graphene-Based Antibacterial Paper." ACS Nano, 2010; 4(7): 4317-4323.
Lacerda et al. "Interaction of Carbon Nanotubes with Human Blood Platelets." NSTI—Nanotech 2010, 2010; 3: 266-269.
Maslov "Nanomaterialy. Podlozhki iz grafena." Perspektivnye tekhnologii, 2010; 17(6): 1, 3 and 4.
Singh et al. "Thrombus Inducing Property of Atomically Thin Graphene Oxide Sheets." ACS Nano, 2011; 5(6): 4987-4996.
Wang et al. "Graphene and graphene oxide: biofunctionalization and applications in biotechnology." Trends in Biotechnology, 2011; 29(5): 205-212.
Written Opinion of the International Searching Authority for International Application No. PCT/US2013/028832 dated Jun. 27, 2013.

* cited by examiner

*Primary Examiner* — Micah Paul Young
(74) *Attorney, Agent, or Firm* — Emory Patent Group

(57) ABSTRACT

Devices and methods relate to inducing or promoting hemostasis. The hemostasis device may include a support layer having a first surface and an opposing second surface. The device may include a layer, the layer disposed on the first surface. The layer may include a target surface configured to contact a target site. The layer may include a monolayer of about 100% graphene or may include laser-reduced graphene oxide. The device may include a sensor configured to measure a level of hemostasis of the target site. The methods relate to a method of manufacturing a hemostatic device including a monolayer of graphene or a layer of laser-reduced graphene oxide.

18 Claims, 6 Drawing Sheets

NANOENHANCED HEMOSTATIC DEVICE AND METHODS FOR MAKING A LAYER HAVING HEMOSTATIC PROPERTIES

CROSS REFERENCE TO RELATED APPLICATION

This application claims priority to U.S. Provisional Application Ser. No. 61/607,429 filed on Mar. 6, 2012, which is hereby incorporated by this reference in its entirety.

BACKGROUND

Despite the clinical availability of several hemostatic agents, the prevalence and clinical burden of bleeding remain considerable. Indeed, the vast majority of trauma-related deaths are due to hemorrhage and given that 50% of patients die within 12 hours of injury, achieving prompt cessation of bleeding is critical to reducing trauma mortality rates. See, e.g., Stewart et al., J Trauma, 2003, 54(1):66-7.

Topical hemostatic agents including chemical agents that promote blood clotting or act as vasoconstrictors; thermal devices that commonly use electrodes, lasers, or heat for cauterization; and mechanical methods that use pressure or ligature to slow bleeding have been used in the combat and civilian settings. See, e.g., Schreiber et al., AORN J., 2011, 94(5):S1-20. However, these systems are only marginally effective in achieving clot formation, are not compliant and therefore unable to treat irregularly shaped wounds, are expensive, are human products that may potentially transmit blood-borne diseases, often require complex and time-consuming preparation, are ineffective in harsh environments or may cause adverse immune reactions. See, e.g., Goodeve et al., Haemophilia, 2010, 16 Suppl 5:79-84.

Therefore, a need exists for new and safe hemostatic agents and devices.

SUMMARY

The disclosure relates to methods and delivery devices for promoting hemostasis at a target site, for example, a wound or opening caused by trauma, a surgical procedure, ulceration, or other cause. The methods and delivery devices include a hemostatic agent that induces platelet binding, including platelet binding and the coagulation of blood.

In some embodiments, the disclosure relates to a device configured to promote hemostasis in a target site of a patient. In some embodiments, the device may include a support layer having a first surface and an opposing second surface; and a layer having hemostatic properties. The layer may be disposed on the first surface, the layer including a target surface configured to contact a target site. The layer may be configured to directly contact the target site.

In some embodiments, the hemostatic agent may be graphene and/or laser-reduced graphene oxide. In some embodiments, the layer may include a monolayer of about 100% graphene. In other embodiments, layer may include laser-reduced graphene oxide. In some embodiments, the device may be configured for topical hemostasis.

In some embodiments, the device may include a closure layer configured to surround the target site. The support layer may be disposed between the closure layer and the layer. In some embodiments, the closer layer may include a fastener configured to contact a region surrounding the target site. In some embodiments, the fastener may include a biocompatible adhesive. In other embodiments, the fastener may include at least one strap.

In some embodiments, the closure layer may be made of a different material than the support layer. In some embodiments, the closure layer may be made of a same material as the support layer.

In some embodiments, the material for the closure layer may include at least one of polyurethane, polypropylene, polyethylene, or silicone estomer, as well as the like. In some embodiments, the material for the support layer and/or closure layer may include woven materials/fabrics, nonwoven materials/fabrics, synthetic materials, and natural materials. In some embodiments, the support layer may include gauze.

In some embodiments, the device may include a sensor configured to measure clot formation. In some embodiments, the senor may be configured to alert a status of the clot formation. In some embodiments, the sensor may include a display disposed on an outer surface of the closure layer. The outer surface of the closure layer may oppose the target skin surface layer.

In some embodiments, the device may include additional layers. In some embodiments, the device may include at least one additional layer between the support layer and the closure layer. In some embodiments, the additional layer may include graphene. In other embodiments, the additional layer may include an agent different from the hemostatic layer. The other agents may include but is not limited to anti-microbial agents, anti-bacterial agents, anti-inflammatory agents, and agents that inhibit free radical formation, and a combination thereof.

In some embodiments, the hemostatic layer may include more than one region. In some embodiments, the first region may include the monolayer of the graphene and the second region may include a different agent.

In some embodiments, the hemostatic layer and the support layer may be of a same length and width (parallel to the skin contact surface). In some embodiments, the hemostatic layer and the support layer may be of different lengths and widths. In some embodiments, the hemostatic layer may partially overlap or cover the support layer. In other embodiments, the hemostatic layer may completely overlap or cover the support layer.

In some embodiments, the disclosure relates to a method of promoting hemostasis in a patient at a target site. In some embodiments, the method may include applying a hemostatic device to the target site. The hemostatic device may include a layer that has hemostatic properties. In some embodiments, the layer may include a monolayer of about 100% graphene. In other embodiments, the layer may include laser-reduced graphene oxide. The method may include applying a surface of the layer directly to the target site so that the hemostatic layer at least partially covers the target site.

In some embodiments, the disclosure relates to a method of manufacturing a graphene structure. The method may include growing at least one graphene film on a foil; and removing the graphene film from the foil, the removing including coating the surface with a solution to dissolve the foil. The method may include transferring the graphene film to a substrate. The solution may be poly-methyl methacrylate (PMMA). In some embodiments, the disclosure may relate to a device include graphene structure manufactured according to this method.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
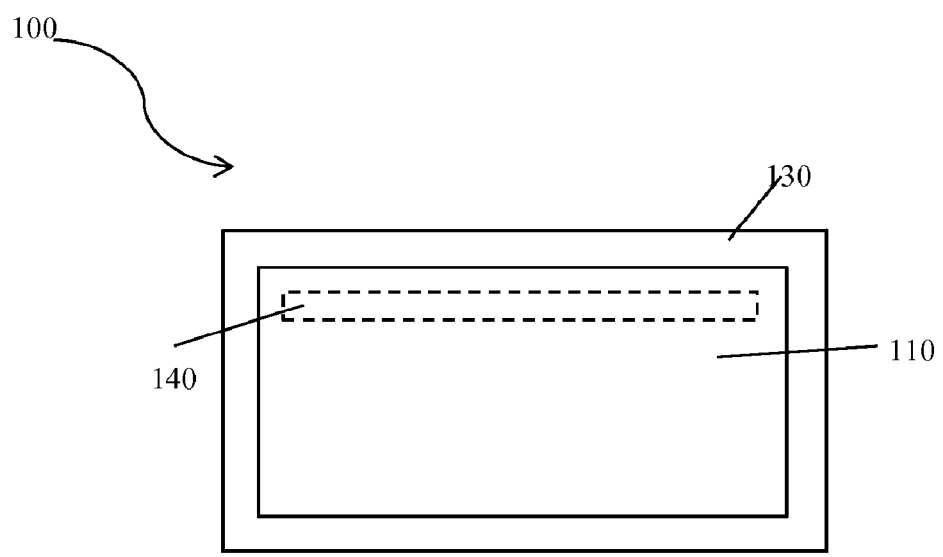
FIG. 1 shows a view of an example of a hemostatic device according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications The disclosed devices and methods relate to promoting or achieving hemostasis by inducing platelet formation. The disclosed devices and methods may relate to promoting or achieving "topical hemostasis." The disclosed devices and methods may induce platelet formation to treat or prevent bleeding in a patient. The source of bleeding may be caused from a medical procedure (e.g., surgery), trauma or wound, such a skin injury or laceration. "Patient" refers to any animal, preferably human, livestock, or a domestic pet. Patients may include a patient that is high risk for life-threatening hemorrhage, for example, patients with over-anticoagulation and coagulopathies, such as hemophilia and von Willebrand disease, and patients with cancer undergoing chemo-therapy or radiotherapy. The devices and methods may result in coagulation of blood. "Hemostatic" or "Hemostatic properties" refers to the ability to stop or minimize bleeding as one skilled in the art of hemostasis would understand those terms to mean (e.g., inducing platelet formation).

In some embodiments, a hemostatic device may include at least one layer (also referred to as "hemostatic layer") having hemostatic properties. In some embodiments, the layer may include a nano-hemostatic agent. The layer may include graphene or reduced graphene oxide. The graphene oxide may be laser-reduced graphene oxide. In some embodiments, the layer may include a single atom layer, i.e., monolayer, of graphene. In some embodiments, the layer may include a sheet or film composed of single atom layer of graphene. In some embodiments, the layer may be about 100% graphene. In some embodiments, the layer may include at least about 15% oxygen content. In some embodiments, the layer may include about 20% oxygen content (e.g., 18-20), 25% oxygen content, 30% oxygen content, 35% oxygen content (e.g., 33-35), etc.

In some embodiments, the layer may include at least one layer of reduced-graphene oxide. In some embodiments, the layer may be a monolayer. In other embodiments, the layer may include a few layers of reduced graphene oxide.

In some embodiments, the graphene oxide may be reduced by a laser (also referred to as "laser-reduced graphene"). Laser-reduced graphene oxide generally has a unique morphology due to not uniform energy distribution of the laser beam. The laser-reduced graphene can have ultra-clean surface compared to chemically reduced graphene oxide. The laser-reduced graphene may be produced by any known methods, including, but not limited to, reduction of a graphene oxide solution by pulsed laser irradiation using, for example, a KrF excimer laser. In other embodiments, the graphene oxide may be reduced by other known methods Graphene is a nanomaterial that has unique mechanical and electrochemical properties. Graphene is a form of carbon arranged in a flat monolayer of atoms tightly packed into a two-dimensional (2D) honeycomb lattice.

Graphene has the following properties: high rigidity coupled with high flexibility, potentially antibacterial properties, and thrombogenicity properties. Graphene has unique mechanical properties of graphene to enable bonding to a base structure, such as gauze, and the uniquely high stiffness in the context of high flexibility of graphene. This may ensure that the material does not break off into the circulation to cause in vivo thrombi.

Graphene and compositions including graphene have been shown to have antibacterial/bacteriostatic properties. See, e.g., Hu et al., ACS Nano., 2010, 4(7):4317-4323. As interest in developing graphene-based materials for medical applications has significantly increased, researchers have begun to evaluate the potential toxicity of these novel nanotechnology platforms for in vivo use. Graphene nanoparticles were found to dramatically induce platelet aggregation and activation, which was associated with inside-out activation of the $\alpha_{IIb}\beta_3$ integrin, activation of nonreceptor Src and syk tyrosine kinases, signaling of phospholipase C-IP$_3$/diacylglycerol-Ca$^{2+}$/protein kinase C transduction pathways, cytoskeletal remodeling, and release of calcium from intracellular stores. See, e.g., Singh et al., ACS Nano, 2011, 5(6):4987-4966. Indeed, the addition of graphene nanoparticles to platelet suspensions induced as much aggregation and activation as full doses of thrombin, one of the most potent platelet agonists.

The layer may include a surface (also referred to as "target surface" or "skin contact surface") configured to directly contact a target site of the patient. The target site may be the site or surface targeted for platelet activation. The target site may include source of bleeding caused from medical procedure, trauma or wound, such a skin injury or laceration.

In some embodiments, a hemostatic device may include at least one support layer (also referred to as base support layer, base layer, or substrate). In some embodiments, the layer may be disposed on the support layer. In some embodiments, the closure layer may entirely surround or partially surround the support layer and/or the layer.

In some embodiments, the support layer may be any biocompatible material. The biocompatible material may be a non-resorbable substrate. In some embodiments, the biocompatible material may be an absorbent material. In some embodiments, the biocompatible material may include but is not limited to woven materials/fabrics, nonwoven materials/fabrics, synthetic materials (e.g., rayon, nylon, lycra, Gore-Tex®), and natural materials (e.g., cotton). Examples of the support layer may include, but is not limited to gauze, cotton balls, an elastomeric layer, and a waterproof film.

In some embodiments, the hemostatic device may include a closure layer. In other embodiments, the closure layer may be configured to surround the wound (e.g., the target site) and seal the wound (target site) so that blood may not escape. In some embodiments, the closure layer may be configured to partially or fully surround the body or appendage that includes the target site. In some embodiments, the closure layer may be integrated with the support layer. In other embodiments, the closure layer may be separate from the support layer.

In some embodiments, the closure layer may include a skin contact surface or target surface. The closure layer and/or the support layer may be made of a material that has a skin contact or target surface that is impermeable to water, blood and/or tissue penetration. The closure layer may be made of materials, such as, but not limited to, polyurethane, polypropylene, polyethylene, silicone estomer, and the like. The closure layer may be made of a flexible material. In some embodiments, the closure layer may be stretchable in at least one direction.

In some embodiments, the hemostatic device may include at least one fastener. In some embodiments, the fastener(s) may include a biocompatible adhesive. The biocompatible adhesive may be disposed on a target surface or skin contact surface. The adhesive may be disposed on the closure layer.

In some embodiments, the fastener(s) may include additionally or alternatively hook, loop fasteners, Velcro, buckles, clamps, or the like. The hemostatic device may include the fasteners on the closure layer and/or at least one strap configured to completely surround the body or appendage. In some embodiments, the strap(s) may be of any fabric. The fabric may include but is not limited to a rubberized or coated, fluid impermeable fabric, or may be sheets of a polymer. In some embodiments, the strap(s) may be flexible. In some embodiments, the strap(s) may be stretchable in at least one direction.

The configuration and shape of the hemostatic device may depend on the wound or bleed to be controlled. For example, the hemostatic device, for example, may be a bandage or a peripheral hemostasis wrap. In some embodiments, the hemostatic device may be configured to exert pressure and force against the target surface to minimize blood loss from the wound. The hemostatic device may also be incorporated into a variety of medical device embodiments including other hemostatic bandages, hemostatic plugs, moist dressings, biological dressings.

Also, the configuration and shape of the hemostatic device may depend on the layer(s) having hemostatic properties. In some embodiments, the hemostatic device may omit or not include the support layer. For example, a hemostatic device may include a layer of laser-reduced graphene oxide without a support layer. The device may include a closure layer and a layer of laser-reduced graphene oxide.

In some embodiments, the shape and size of the layers may be configured based on the wound or bleed to be controlled. For example, the device may have a triangular or rectangular shape.

Figure 2:
FIG. 2 shows another view of the example.
Figure 6:
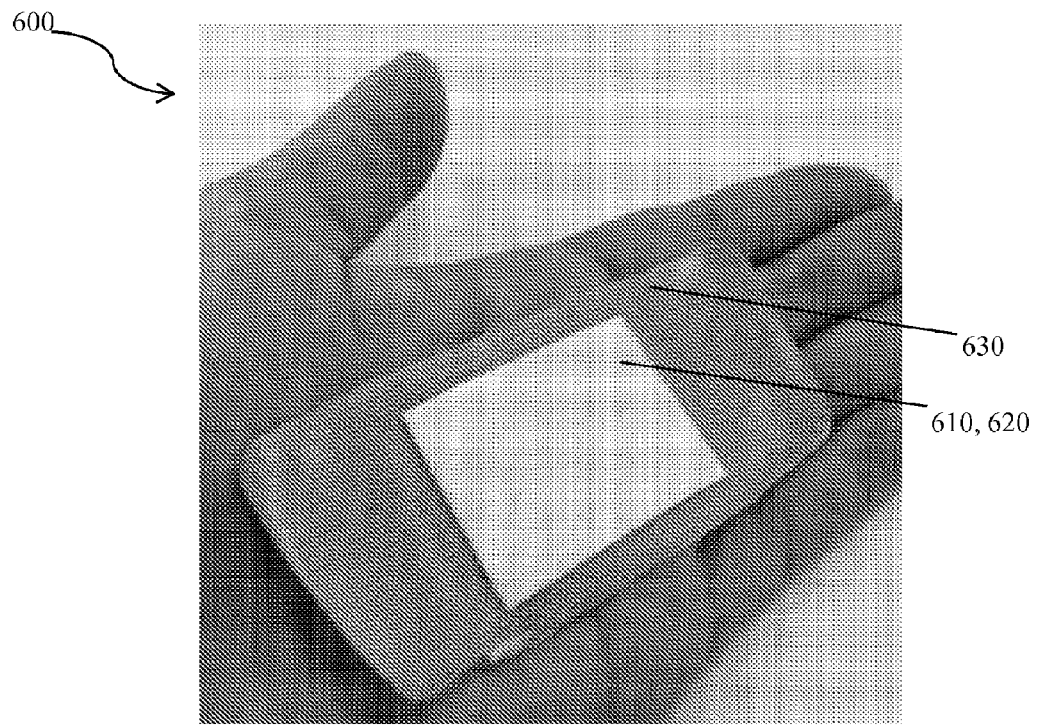
FIG. 6 shows an example of a hemostatic device according to embodiments.

FIGS. 1, 2, and 6 show examples of a hemostatic device according to embodiments. As shown in FIGS. 1 and 2, hemostatic device 100 may include a layer 110 having hemostatic properties (also referred to as "hemostatic layer") disposed on the support layer or substrate 120. The support layer 120 may be disposed on a closure layer 130. It should be understood that the device shown is not drawn to scale. The layer 110 may be invisible to the human eye.

In some embodiments, the layer may be disposed along the entire support layer. In other embodiments, the layer may be disposed along a portion of the support layer. In some embodiments, the layer may include more than one region disposed on the support layer. In some embodiments, the layer may include two or more regions disposed on the support layer. In some embodiments, the support layer may include additional agents, for example, anti-microbial agents. These additional agents may be disposed at region(s) different from the region(s) that include the layer In some embodiments, the closure layer may be larger than the layer and/or support layer. In some embodiments, the closure layer, the layer, and base layer may have the same shape, different shape, or a combination thereof.

In some embodiments, the hemostatic device may include additional agents, for example, that promote wound-healing. The agents may include but are not limited to anti-microbial agents, anti-bacterial agents, anti-inflammatory agents, and agents that inhibit free radical formation, and a combination thereof.

Anti-inflammatory agents may be agents that inhibit or prevent an immune response in vivo. The agents may include but are not limited to (i) agents that inhibit leukocyte migration into the area of surgical injury ("leukocyte migration preventing agents"); and (ii) anti-histamines. Representative leukocyte migration preventing agents may include but is not limited to silver sulfadiazine, acetylsalicylic acid, indomethacin, and Nafazatrom. Representative anti-histamines may include but is not limited to pyrilamine, chlorpheniramine, tetrahydrozoline, antazoline, and other anti-inflammatories such as cortisone, hydrocortisone, betamethasone, dexamethasone, fluocortolone, prednisolone, triamcinolone, indomethacin, sulindac, its salts and its corresponding sulfide, and the like.

Representative agents that inhibit free radical formation may include but is not limited to antioxidants that inhibit the formation and/or action of oxide products, superoxide dismutase (SOD), catalase, glutathione peroxidase, b-carotene, ascorbic acid, transferrin, ferritin, ceruloplasmin, and desferrioxamine .alpha.-tocophenol.

Anti-bacterial and anti-microbial agents may include but are not limited to antibacterial substances such as .beta.-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxican; iodine; beta dine; and the antimicrobial combination of fluoroalanine/pentizidone; nitrofurazones, and the like.

The other hemostatic agents may include but are not limited to procoagulant enzymes, proteins and peptides, can be naturally occurring, recombinant, or synthetic, and may be selected from the group consisting of prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof.

In some embodiments, the closure layer and/or the support layer may include additional agents. In the other embodiments, the hemostatic device may include additional layers that include the additional agents.

For example, in some embodiments, the hemostatic device may include additional layers (at least one another layer) between the layer (110) and the closure layer (130). In some embodiments, these layers may include the additional agents. The layers may include a layer of the additional agent and a support layer. In some embodiments, the hemostatic device may include an anti-microbial layer between the support layer and the closure layer. The anti-microbial layer may include a microbial nanoparticle. In some embodiments, the hemostatic device may include a second layer of graphene (disposed on a second support layer) between the support layer (120) and the closure layer (130).

In some embodiments, the hemostatic device may include at least one sensor. The sensor may include at least one biosensor configured to measure clot formation. The sensor may be configured to measure clot formation by measuring graphene resistance.

The sensor may be disposed anywhere on the surface. The sensor may be configured to read a portion or an entire layer having hemostatic properties. As shown in FIG. 1, the device 100 may include a sensor 140. Although one sensor is shown as disposed on device 100, the hemostatic device may include more than one sensor. The hemostatic device may include more than one sensor, each sensor configured to measure the clot formation in a specific region corresponding to the layer.

In some embodiments, the sensor may be configured to alert the status of the clot formation, for example, when hemostasis is achieved. The sensor may include a display on the external surface of the hemostatic device (opposing the target surface) to display the status of the hemostasis or clot formation. In other embodiments, the display may display the amount or percentage level of clot formation. In some embodiments, the display may change colors based on the level or percentage of clot formation.

In some embodiments, the biosensor may be configured to communicate with another device external to the hemostatic device. For example, the display may be provided on a wireless handheld device, for example, a smart phone or tablet.

Figure 3:
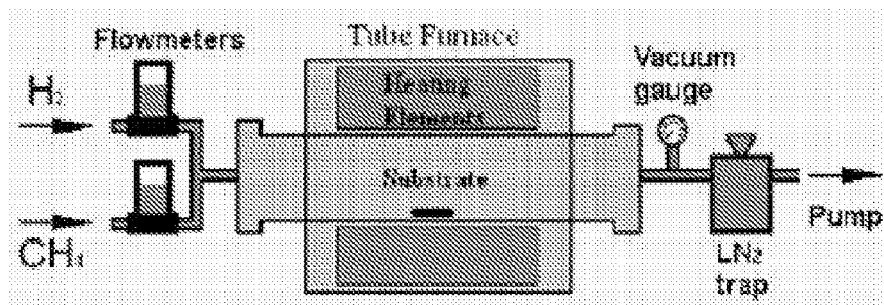
FIG. 3 shows a schematic of chemical vapor deposition for the hemostatic layer according to embodiments.

Methods of Making a Graphene/Reduced Graphene Oxide Structure Having Hemostatic Properties and Hemostatic Device In some embodiments, a graphene structure (e.g., layer) can be made according to the method shown in FIG. 3. FIG. 3 shows an example of a method 300 of synthesizing a layer composed of about 100% graphene. First, single atom layers of graphene may be synthesized via chemical vapor deposition of $CH_4$ and $H_2$ using a protocol discussed in Cao et al., Appl. Phys. Lett., 2010, 96, 122106 and Sidirov et al., Appl. Phys. Lett., 2011, 99, 013115, which are incorporated by reference in their entirety. Next, graphene films may be grown on 25-μm thick copper foils in a high temperature furnace. The foils may have a surface area of about 10 cm$^2$, but the surface may be increased if needed. Then, the graphene may be removed from the Cu foils by etching in an aqueous solution of iron nitride. The surface of the graphene-on-Cu may be coated with poly-methyl methacrylate (PMMA) and after the Cu is dissolved, the PMMA graphene may be lifted from the solution and can be transferred and bonded to any substrate or base layer for example, a bandage gauze. The graphene layer may be about 0.34 nm thick. At the atomic level, van der waals forces may be strong enough to keep the graphene on the base layer without requiring an additional adhesion layer or step. In other embodiments, the graphene layer may have different concentrations and may be made by different methods.

In some embodiments, a reduced graphene oxide structure (e.g., layer) may be laser-reduced. The laser-reduced graphene may be produced by any known methods, including, but not limited to, methods related to reduction of a graphene/graphite oxide solution by pulsed laser irradiation using, for example, a KrF excimer laser. In other embodiments, the reduced graphene oxide structure may be reduced by other known methods.

In some embodiments, the layers or films of graphene or reduced graphene oxide produced may be used for medical purposes, such as hemostatic devices. In other embodiments, the layers or films of graphene produced may be for other purposes, such as electrical applications (e.g., electrodes, solar cells, transistors, display screens, sensors (e.g., chemical sensors and medical sensors to diagnose diseases, batteries (e.g., lithium-ion batteries and ultracapacitors), circuit boards, semiconductors). For example, the layer produced may be transferred and bonded to a substrate, such as circuit board.

Figure 4:
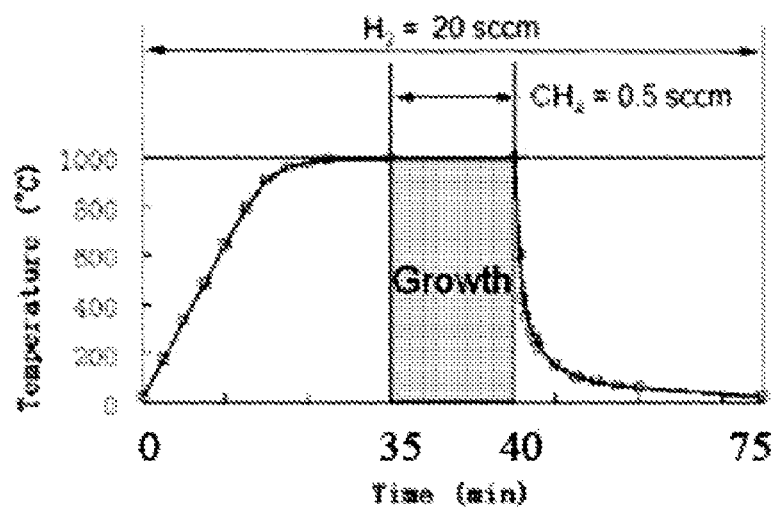
FIG. 4 shows time dependence graph of experimental parameters.

FIG. 4 shows a time dependence graph 400 of experimental parameters: temperature and gas flow rate for synthesizing a layer of graphene.

Figure 5:
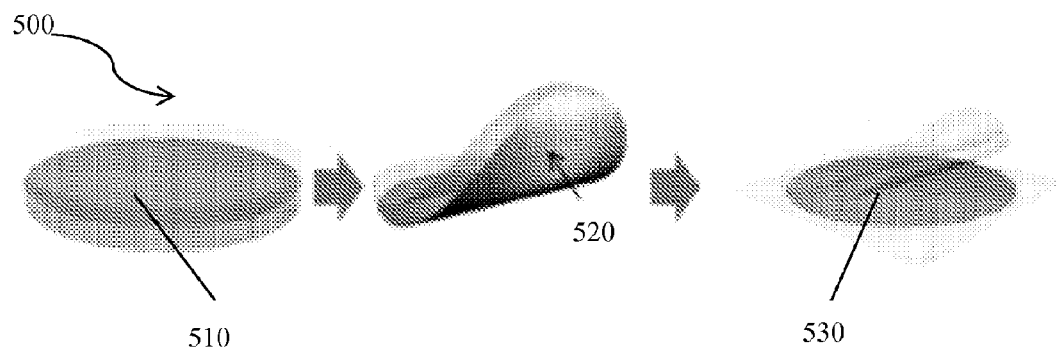
FIG. 5 shows a method of manufacturing a hemostatic device.

FIG. 5 shows a method 500 of manufacturing a hemostatic device according to embodiments. In some embodiments, in step 510, a layer (an area of graphene), may be etched and transferred onto a base or substrate layer. In some embodiments, in step 520, the graphene 510 may be etched with FeCle$_3$ to obtain a graphene on PMMA. After, in step 530, the graphene may be transferred and the PMMA may be dissolved to produce a hemostatic device.

In some embodiments, the disclosure may relate to a method of treating a wound in a mammalian, the mammalian having a skin injury or laceration. The method may include applying the hemostatic device to a mammal. The applying may include disposing the hemostatic layer directly onto a target site of the patient, for example, the skin injury or laceration. The method may include inducing platelet formation.

Some embodiments of the disclosure may be illustrated by one or more of the examples provided herein.

Example 1

FIG. 6 shows an example of a hemostatic device according to embodiments. The hemostatic device 600 is a bandage. The hemostatic device 600 includes a layer 610 having hemostatic properties. In some embodiments, the layer 610 may be a monolayer sheet of about 100% graphene. The graphene sheet, which is one atom thick, is invisible to the naked eye. In other embodiments, the layer 610 may include reduced graphene oxide. In some embodiments, the layer may be a monolayer and/or a plurality of layers of reduced graphene oxide. In some embodiments, the layer may be laser-reduced graphene oxide. The hemostatic device 600 includes a support layer 620 that is gauze. The hemostatic device 600 also includes a closure layer 630 that includes an adhesive. In some embodiments, the hemostatic device 600 may omit the support layer 620.

Figure 7:
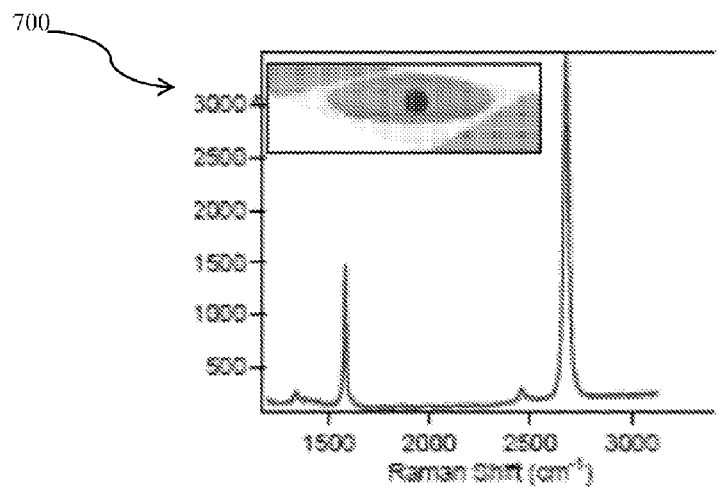
FIG. 7 shows a Raman spectrum of the example.

Because the graphene sheet is invisible to the naked eye, high precision techniques such as Raman spectroscopy detected and confirmed the presence of graphene on the bandage gauze. FIG. 7 shows results of Raman spectrum 700 of the example shown in FIG. 6. The spectrum shows signature Raman peaks for graphene, i.e., the G'-band is about 2680 cm$^{-1}$, the G-band is about 1588 cm$^{-1}$ and the D-band is about 1345 cm$^{-1}$. The red dot in FIG. 7 indicates the position of the Raman laser spot (image is not scaled to real dimensions). As only graphene shows Raman spectra and no Raman signal is obtained from the materials used in gauze, this data confirms the presence of graphene on the example device.

Example 2

To confirm that the protocol to transfer and coat graphene onto various substrates, as shown in FIGS. 3-5, enhances platelet activation, standard glass coverslips were coated with single-atom thick graphene sheets and a standard platelet adhesion assay was conducted. Specifically, human platelets were isolated from human blood using standard techniques, stained with a fluorescent cell membrane dye, and then exposed to glass coverslips that were either coated with graphene or not (control). Interestingly, the data indicates that coating a single atomic layer of graphene onto glass enhances platelet adhesion by about 6 fold (FIGS. 8 and 9).

Figure 8:
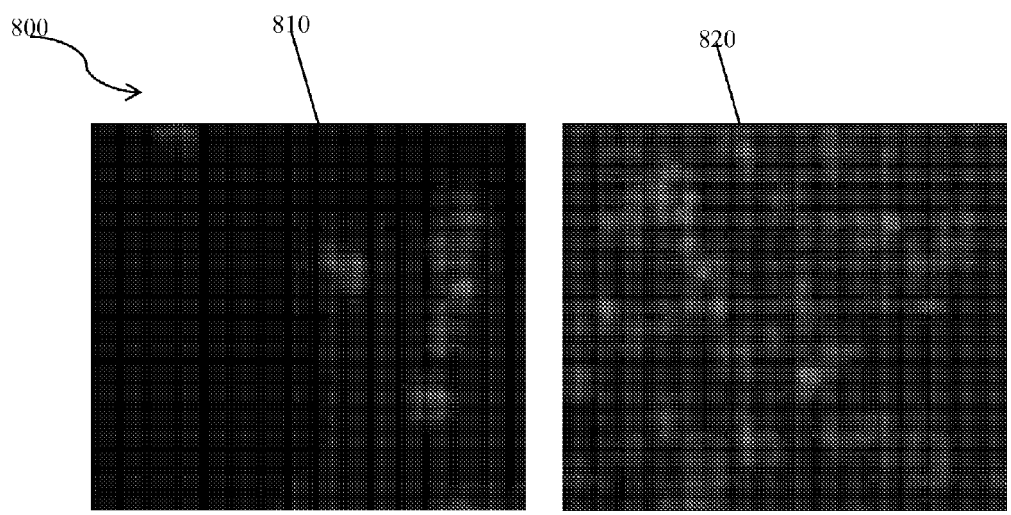
FIG. 8 shows sample images of a platelet adhesion on a graphene-coated glass.
Figure 9:
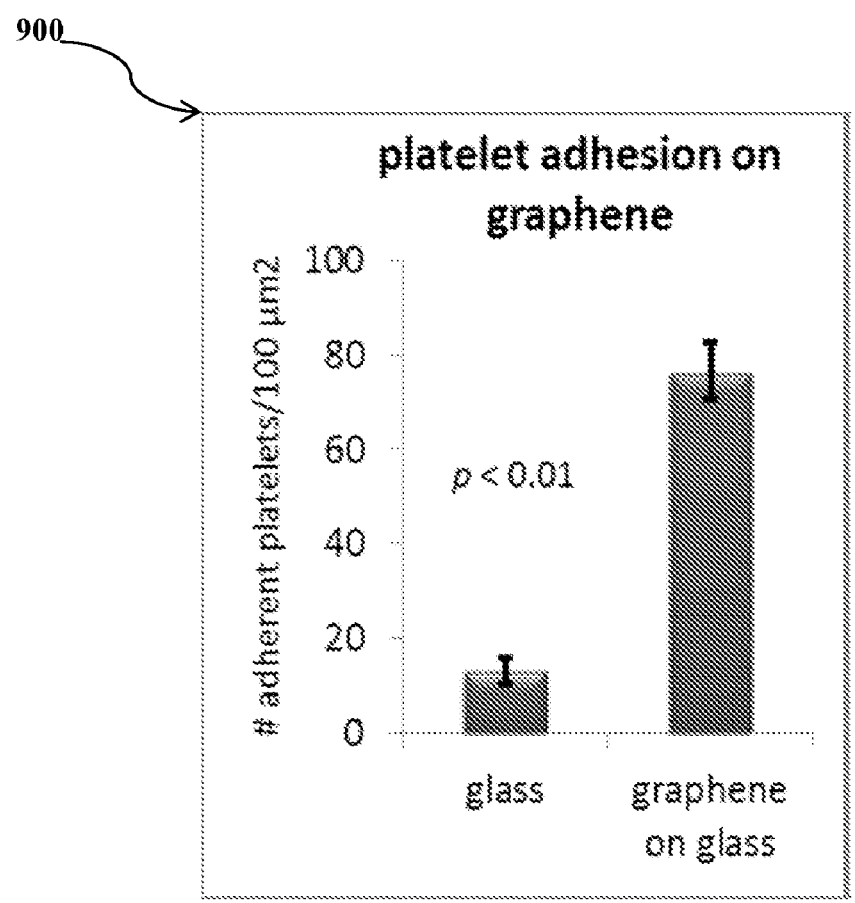
FIG. 9 shows a quantification and Mann Whitney analysis of the graphene coated glass.

FIG. 8 shows images 810 and 820 of the platelet adhesion on graphene-coated glass. Sample images 810 and 820 taken via epifluorescence microscopy of platelets (stained fluorescently with a cell membrane) expectedly show some baseline adhesion on unblocked, bare glass coverslips. Platelet adhesion in image 820 on graphene-coated glass coverslips is dramatically increased when compared to the control conditions of those seen in image 810. Both scalebars=10 µm. FIG. 9 shows a quantification and Mann Whitney analysis 900 that reveal an increase in platelet adhesion by about 6 times when a single atom layer of graphene is coated onto the glass surface and that this difference is statistically significant.

Of note, these coverslips were not coated with any other ligands (e.g., collagen, fibrinogen) that are typically used to study platelet adhesion. Overall, these experiments indicate that coating graphene onto substrates such as bandage gauze will enhance clot formation on those surfaces and materials.

Example 3

Figure 10:
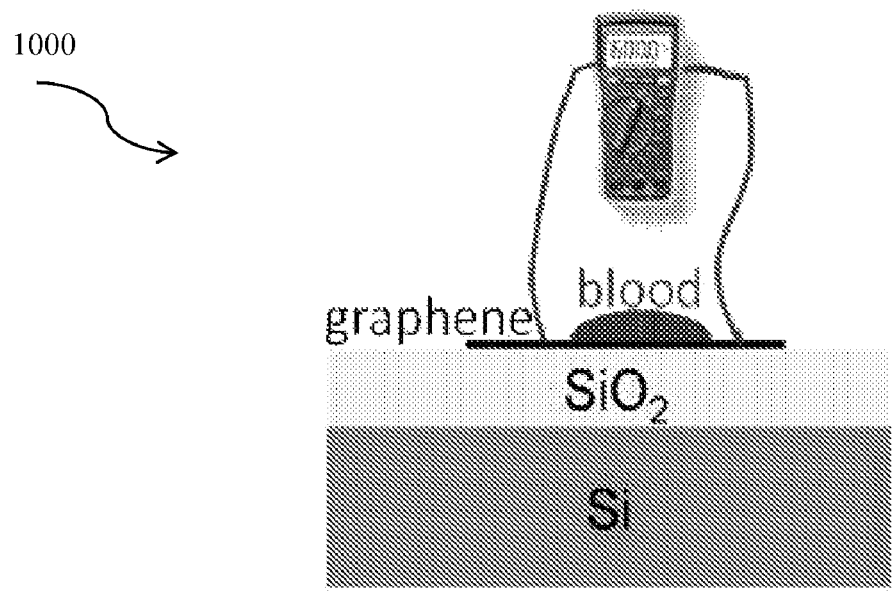
FIG. 10 shows a schematic of a resistance measurement configuration.

One of many of graphene's unique properties is its extreme electrical sensitivity to its surroundings, enabling it to be an ideal electrochemical biosensor. FIG. 10 shows a schematic 1000 of the resistance measurement set-up consisting of a layer of graphene deposited on Si/SiO$_2$ substrate and four aluminum leads.

Figure 11:
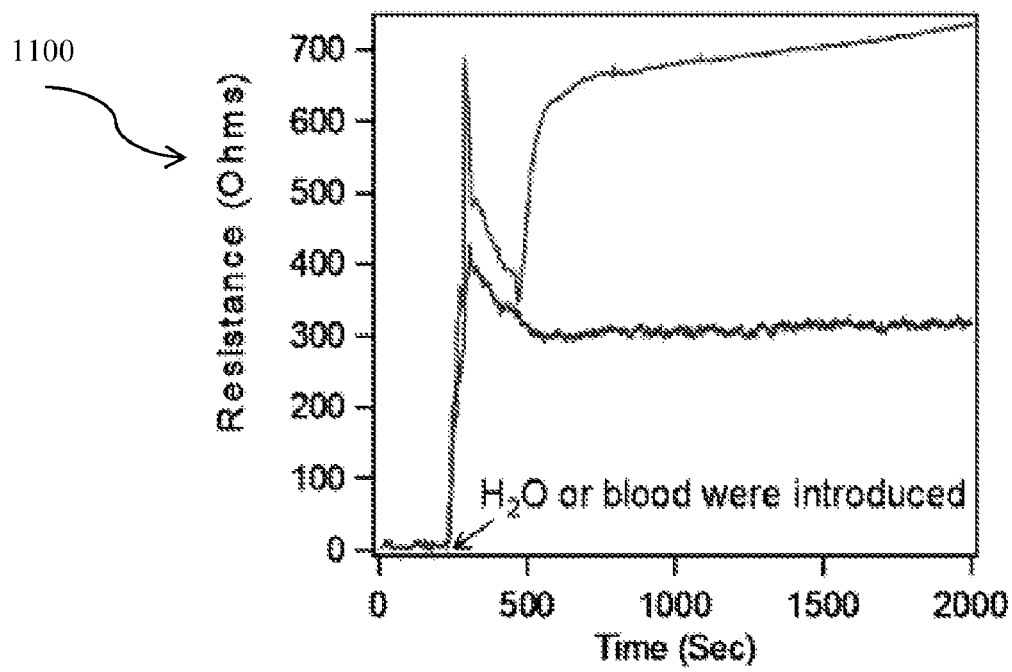
FIG. 11 shows a graphene resistance curve.

It has been recently observed that a 4 cm$^2$ area of graphene may detect clot formation within a single drop of blood ex vivo (FIG. 11). FIG. 11 shows a comparison 1100 of graphene resistance over time upon exposure to DI water (blue curve) and fresh human whole blood (red curve).

When compared to water, clotting whole blood in contact with the graphene substrate leads to a dramatic change in resistance. Specifically, upon exposure to a drop of pure DI water, graphene's resistance drastically changes and over minutes, achieves a steady state (FIG. 11). In contrast, upon exposure to a drop of fresh whole blood, the resistance of the graphene patch has an even more pronounced change. In addition, as clot formation ensues (confirmed visually), the resistance curve again drastically increases and plateaus as the clot is fully formed, which is not seen in the control (water) condition. This enables a hemostatic device including graphene, e.g., a graphene bandage, to function not only as a hemostatic agent, but also potentially as a biosensor for clot formation underneath the bandage.

All references cited herein are hereby incorporated by reference in their entirety.

While various embodiments of the disclosure have been described, the description is intended to be exemplary rather than limiting and it will be appeared to those of ordinary skill in the art that may more embodiments and implementations are possible that are within the scope of the disclosure.

What is claimed:

1. A device configured to promote hemostasis in a target site of a patient, comprising:
    a support layer that is a non-absorbable layer having a first surface and an opposing second surface;
    a layer having hemostatic properties, the layer disposed on the first surface, the layer being a monolayer of graphene or graphene oxide and including a target surface configured to contact a target site; and
    one or more sensors configured to measure clot formation on the layer by measuring graphene resistance, the one or more sensors being configured to alert a status of the clot formation.

2. The device according to claim 1, wherein the layer includes a monolayer of about 100% graphene.

3. The device according to claim 1, wherein the layer includes laser-reduced graphene oxide.

4. The device according to claim 3, wherein the graphene oxide includes at least 15% oxygen content.

5. The device according to claim 1, further comprising:
    a closure layer configured to surround the target site, the closer layer including a fastener configured to contact a region surrounding the target site.

6. The device according to claim 5, wherein:
    the closure layer and the support layer are made of different materials; and
    the closure layer includes a fastener.

7. The device according to claim 5, wherein the closure layer is made of a same material as the support layer.

8. The device according to claim 6, wherein the closure layer includes at least one of polyurethane, polypropylene, polyethylene, or silicone estomer.

9. The device according to claim 1, wherein the support layer includes woven materials/fabrics, nonwoven materials/fabrics, synthetic materials, and natural materials.

10. The device according to claim 1, wherein the support layer includes gauze.

11. The device according to claim 5, further comprising:
    another layer between the support layer and the closure layer.

12. The device according to claim 11, wherein the other layer includes graphene.

13. The device according to claim 11, wherein the other layer includes an agent different from the layer.

14. The device according to claim 1, wherein the layer includes more than one region, one region includes the graphene and the other region includes a different agent.

15. A device configured to promote hemostasis in a target site of a patient, comprising:

a support layer that is a non-absorbable layer;
a layer having hemostatic properties disposed on the support layer, the layer being a monolayer of 100% graphene, the layer including a target surface configured to contact a target site; and
one or more sensors configured to measure clot formation on the layer associated with the target site.

16. The device according to claim 15, wherein:
the one or more sensors is configured to measure clot formation by measuring graphene resistance; and
the one or more sensors is configured to alert a status of the clot formation.

17. A method for promoting hemostasis in a patient at a target site, comprising:
applying a hemostatic device to a target site to induce platelet formation, the hemostatic device including:
a support layer that is a non-absorbable layer having a first surface and an opposing second surface;
a layer having hemostatic properties, the layer disposed on the first surface, the layer being a monolayer of 100% graphene and including a target surface configured to contact a target site; and
one or more sensors configured to measure clot formation on the layer associated with the target site; and
wherein the applying includes applying the target surface of the layer directly to the target site so that the layer at least partially covers the target site.

18. The method according to claim 17, further comprising:
measuring clot formation on the layer associated with the target site using the one or more sensors.

* * * * *